US006718011B2

(12) United States Patent
Spahn

(10) Patent No.: US 6,718,011 B2
(45) Date of Patent: Apr. 6, 2004

(54) PLANAR IMAGE DETECTOR FOR ELECTROMAGNETIC RAYS, PARTICULARLY X-RAYS

(75) Inventor: Martin Spahn, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/199,597

(22) Filed: Jul. 19, 2002

(65) Prior Publication Data

US 2003/0016788 A1 Jan. 23, 2003

(30) Foreign Application Priority Data

Jul. 20, 2001  (DE) .......................... 101 35 427

(51) Int. Cl.$^7$ ................................ H05G 1/64
(52) U.S. Cl. ...................... 378/98.8; 378/98.7
(58) Field of Search ................ 378/98.8, 98.2, 378/98.11, 98.12, 207, 98.7

(56) References Cited

U.S. PATENT DOCUMENTS 5,617,461 A    4/1997  Schreiner
5,786,597 A  * 7/1998  Lingren et al. ........ 250/370.09
6,002,743 A  * 12/1999 Telymonde ................ 378/98.8
6,023,533 A  * 2/2000  Sano et al. ................ 382/274
6,028,913 A  * 2/2000  Meulenbrugge et al. ... 378/98.8

FOREIGN PATENT DOCUMENTS

DE   196 40 999   4/1998
DE   199 15 851   7/2000

* cited by examiner

*Primary Examiner*—Toan Ton
*Assistant Examiner*—Richard Kim
(74) *Attorney, Agent, or Firm*—Schiff Hardin LLP

(57) ABSTRACT

In an X-ray diagnostics installation having an X-ray tube, an X-ray generator, a planar solid state X-ray image converter for generating X-ray images that is composed of a number of individual detectors abutting one another, an image system and having a playback device, for avoidance of the abutting locations of the individual detectors being visible in the resulting image, the amplitude of continuously changing gray scale levels at the abutting locations is locally recognized and generates a correction signal is generated corresponding to the amplitude of the gray scale levels. Based on this correction signal the gray scale levels at the abutting locations within a region.

10 Claims, 9 Drawing Sheets

PLANAR IMAGE DETECTOR FOR ELECTROMAGNETIC RAYS, PARTICULARLY X-RAYS

BACKGROUND OF THE INVENTION

1. Field of the Invention

The present invention is directed to an X-ray diagnostics installation of the type having an X-ray tube, an X-ray generator, a planar solid state X-ray image converter for generating X-ray images that is composed of a number of individual detectors abutting one another, an image system and a playback device.

2. Description of the Prior Art

Solid state detectors utilized in X-ray imaging are based on active readout matrices of, for example, amorphous silicon (a-Si). The image information is converted in an X-ray converter (for example, cesium iodide, CsI), is stored as electrical charge in the photodiodes of the matrix, and is subsequently read out via an active switch element with a dedicated electronics and is analog-to-digitally converted.

Solid state detectors (FD) utilized in X-ray imaging are based on active readout matrices of, for example, amorphous silicon (a-Si). The image information is converted in an X-ray converter (for example, cesium iodide, CsI), is stored as electrical charge in the photodiodes of the matrix, and is subsequently read out via an active switch element with a dedicated electronics and is analog-to-digitally converted.

FIG. 1 shows such an X-ray diagnostics installation disclosed by German OS 195 27 148 having an X-ray tube 2 supplied with high-voltage and filament voltage by a voltage generator 1. The X-ray tube 2 emits a conical X-ray beam 3 that penetrates a patient 4 and generates a radiation image on a solid state detector that is sensitive to X-radiation 3. The output signal of the solid-state detector, the image data 6, is supplied to an image system 7. The image system 7 can include converters, image memories and processing circuits. The image system 7 is connected to a monitor 8 for the playback of the acquired X-ray images. Operating elements 9 are connected to the other components of the X-ray diagnostics installation via a system control and communication 10.

FIG. 2 shows a cross-section of the solid state detector 5. The basic components of the solid state detector 5 are a solid state pixel matrix, line drivers and amplifiers. The solid state pixel matrix is in turn composed of a layer with a scintillator 11, for example of cesium iodide (CsI), that supplies in the visible photons spectrum to a pixel matrix 12 of amorphous silicon when irradiated with the X-ray beam 3, photons forming a visible X-ray image. As shown enlarged in FIG. 2, each of the pixels or picture elements of this pixel matrix 12 is composed of a photodiode 13 and a switch 14 that is connected to row lines 15 and column lines 16. The pixel matrix 12 is applied on a glass substrate 19.

All pixels of a line are addressed and read out simultaneously by the line drivers. The signals are processed in parallel in a number of amplifiers 18. In the simplest case, an image is progressively read out line-by-line.

Large-area detectors, for example for general radiography, are generally manufactured of a number of plates, i.e. individual detectors with glass substrates and an a-Si layer in order to maximize the yield and avoid the considerable costs for larger systems. Detectors composed of two or four individual plates are standard. Since two plates always differ in detail in terms of their electrical properties and are also driven by different electronics, non-linearities that make the various plates visible in corrected images can arise under certain conditions. Due to the large "correlated" structures the minutest differences in gray scale value are already visible beginning with a digital unit (du). Further, the differences in gray scale value are generally not described by a single offset per plate but are dependent on the local dose and on the physical characteristics of the plates themselves, so that continuous changes in gray scale value difference (gray scale levels) can occur at a plate-to-plate transition. These differences in gray scale value generally occur non-deterministically.

German OS 199 15 851 discloses a method for processing the pixel image signals supplied by a solid state image sensor composed of a pixel matrix with a dark reference zone, whereby an offset correction value is formed from the dark reference zone.

German OS 196 40 999 discloses a method for covering errors in images encoded by blocks, whereby a correction at the block edges is estimated by a straight line or a polynomial.

SUMMARY OF THE INVENTION

An object of the present invention is to provide an X-ray diagnostic installation of the type initially described wherein a uniform transition arises at the abutting locations of the plates and the butting structure—the abutting locations of the plates—is no longer visible.

The object is inventively achieved in an image system having a detection unit that locally recognizes the amplitude of continuously changing gray scale levels at the abutting locations and generates a correction signal corresponding to the amplitude of the gray scale levels, and a correction unit for the continuous adaptation of the gray scale levels at the abutting locations. As a result, continuous changes in gray scale that occur between two plates, i.e. along an abutting location, can be corrected such that the abutting location of the plates is no longer optically visible—i.e. can no longer be perceived. To that end, the abutting locations between the respective plates are made uniform of smoothed steady in the gray scale transition. Without this method, the plates are generally visible due to different gray scales, which is an important disadvantage compared to a manufacturer who can manufacture the detectors from a single plate. The special characteristic of the method is that the gray scale matching at the abutting location is locally undertaken, and thus different gray scale levels at different locations can be taken into consideration. The apparatus analyzes the current image and is suitable for non-deterministic gray scale value transitions.

Inventively, the detection unit can include a subtraction stage, an averaging stage and/or a filter stage.

It has proven advantageous when the correction unit includes a multiplication stage for multiplying the correction factor of the detection unit by a location-dependent factor within a region. The multiplication unit can thereby multiply the correction factor by an x-dependent or y-dependent function that decreases steadily proceeding from the abutting location.

The detection unit can include an addition stage that is connected to the multiplication stage.

The correction can be manually influenced by allowing the size of the region, i.e. the range of the correction, to be adjustable.

Inventively, the solid state X-ray image converter can be composed of two individual detectors having only one abutting edge, or of four individual detectors having two abutting edges that form a cross of abutting edges. Other arrangements are also conceivable, for example one having 3*3 individual detectors as well.

DESCRIPTION OF THE PREFERRED EMBODIMENTS

Figure 1:
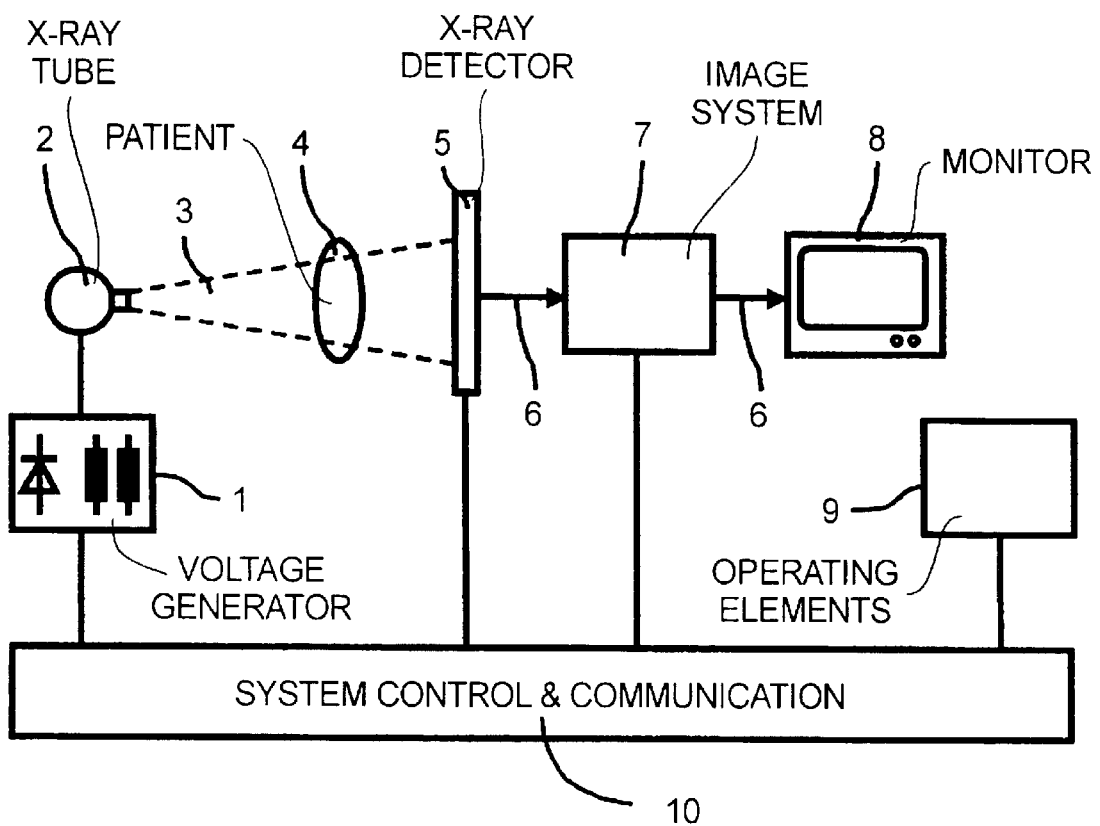
FIG. 1, as noted above, is a block diagram a known X-ray diagnostics installation with an X-ray detector.
Figure 2:
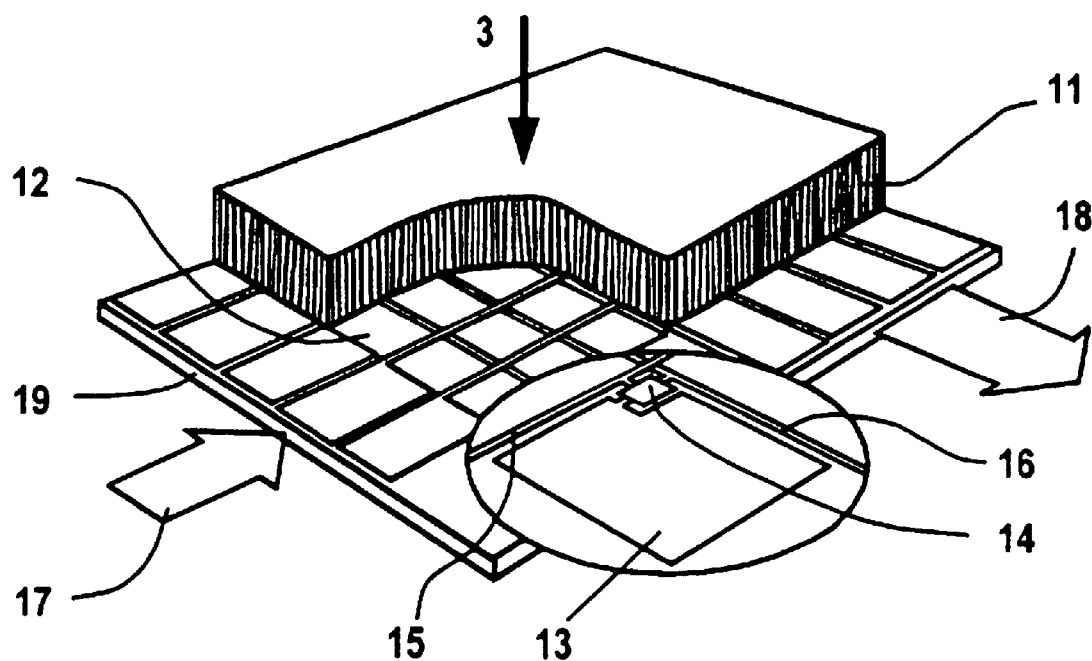
FIG. 2, as noted above, is a perspective view of a known X-ray detector.
Figure 3:
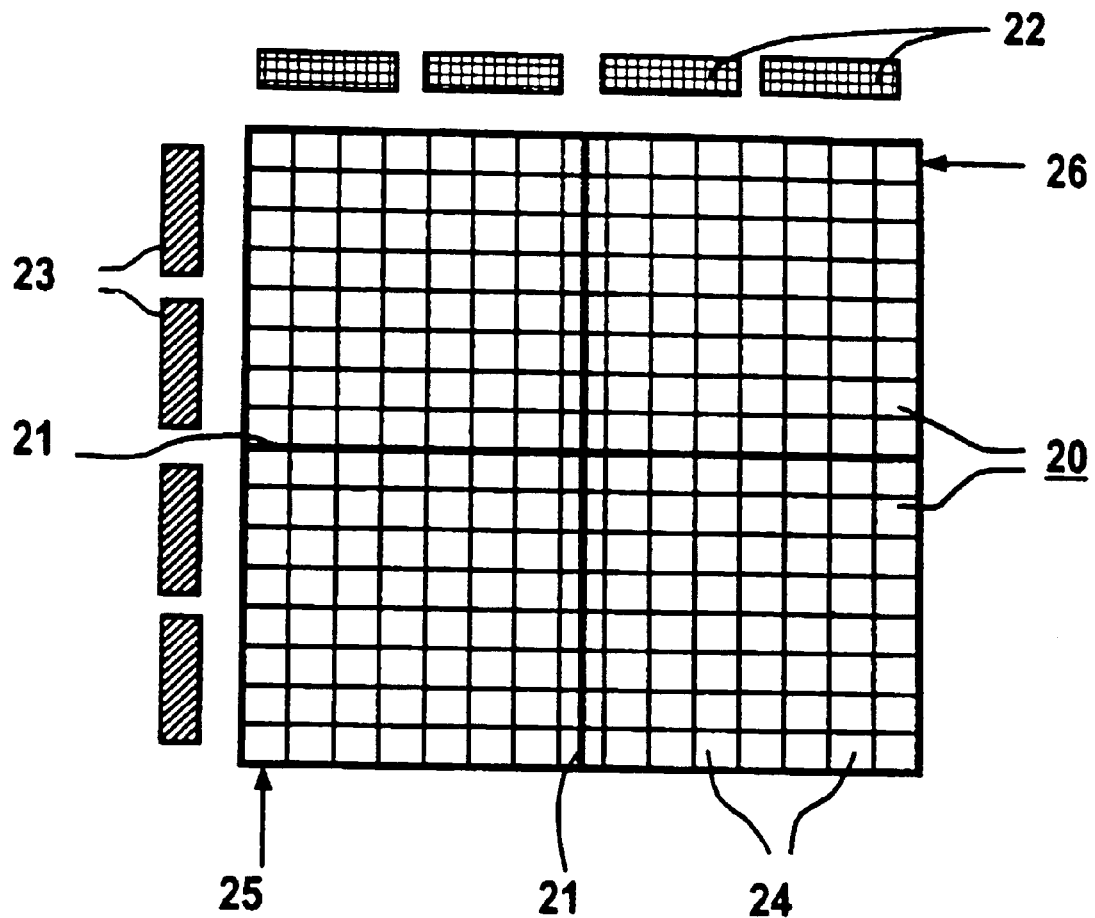
FIG. 3 is a schematic view of a flat image detector composed of four individual plates with a cross of abutting edges.

FIG. 3 shows a schematic view of a plat image detector that is composed of four a-Si plates. These touch one another at the abutting edges 21. For readout of the image information from the pixel matrix 12, readout chips 2 and drive chips 23 are connected to the active pixel matrix 12 via, for example, flexible interconnects (not shown). The pixel elements 24 are arranged in columns 25 and rows 26.

Figure 4:
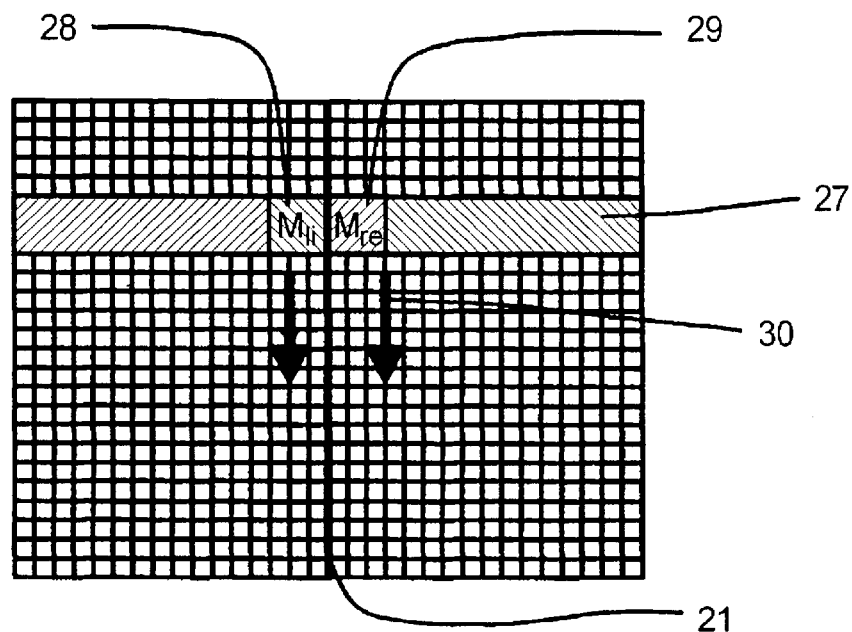
FIG. 4 illustrates measurement of the local discontinuity in gray scale value in a plan view onto the panels.
Figure 5:
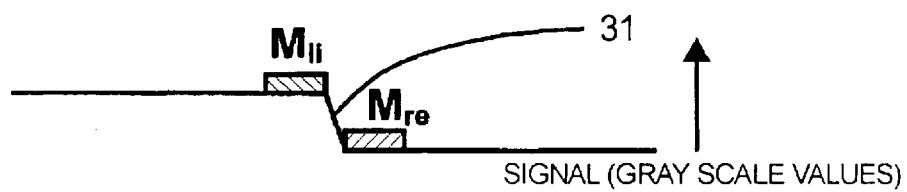
FIG. 5 illustrates measurement of the local discontinuity in gray scale value in a presentation of the signal.
Figure 6:
FIG. 6 illustrates gray scale level after local correction.

The problem and the inventive solution thereof shall now be explained in greater detail on the basis of FIGS. 4 through 6. Contrast discontinuities in the local gray scale values can occur at an abutting edge 21 of two plates 20. The region 27 is observed for this purpose, whereby measurement ranges $M_{le}$ 28 and $M_{ri}$ 29 are defined in the proximity of the abutting edge 21. The scan direction is referenced 30. FIG. 5 shows the measured signal of the gray scale values with the local gray scale value discontinuity. The curve shows that the gray scale value signal has a discontinuity 31 given nearly the same brightness. This discontinuity 31 in the gray scale value signal is noticeable as a brightness difference in the image and is disturbingly visible. Under the same conditions, FIG. 6 shows the gray scale value signal after the inventive correction of the local gray scale value level. The signal is averaged such in the region of the abutting edges 21 that, as shown, seamless transitions that do not lead to any visible change of the gray scale value in the X-ray image can be created.

Figure 7:
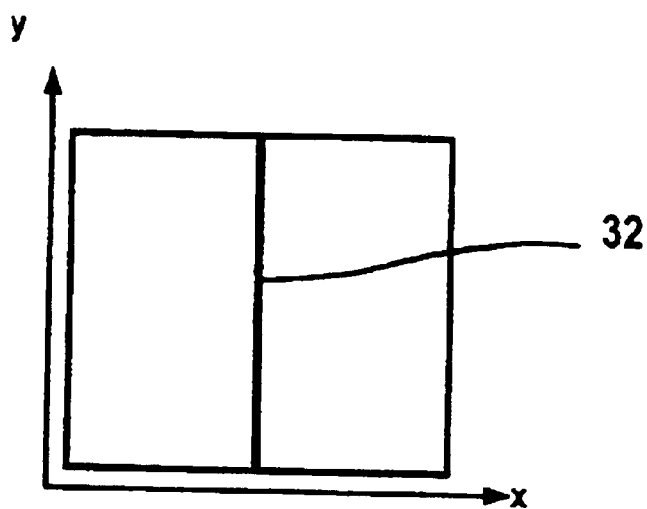
FIG. 7 shows measurement arrangement for an abutting location.
Figure 8:
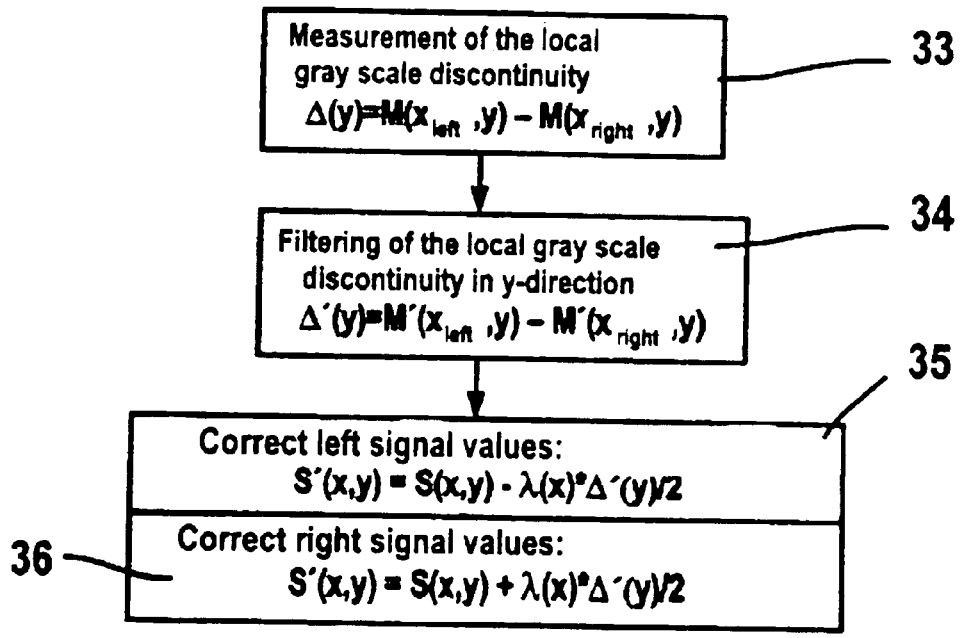
FIG. 8 is a flowchart measurement and correction procedure for an abutting location in the y-direction.

The measurement and correction procedure for an abutting location 32 (FIG. 7) in y-direction is now explained in greater detail on the basis of FIGS. 7 and 8. First, a measurement 33 of the local gray scale value discontinuity in the region of the abutting location 32 ensues according to Equation (1).

$$\Delta(y)=M(x_{left}, y)-M(x_{right}, y) \qquad (1)$$

Subsequently, a filtering 34 of the local gray scale value discontinuity in y-direction is implemented according to Equation (2).

$$\Delta'(y)=M'(x_{left}, y)-M'(x_{right}, y) \qquad (2)$$

After this pre-processing, the correction 35 of the signal values to the left of the abutting location ensues first according to Equation (3):

$$S'(x,y)=S(x,y)-\lambda(x)*\Delta'(y)/2 \qquad (3)$$

and then (36) ensues to the right of the abutting location 32 according to Equation (4):

$$S'(x,y)=S(x,y)+\lambda(x)*\Delta'(y)/2 \qquad (4).$$

Figure 9:
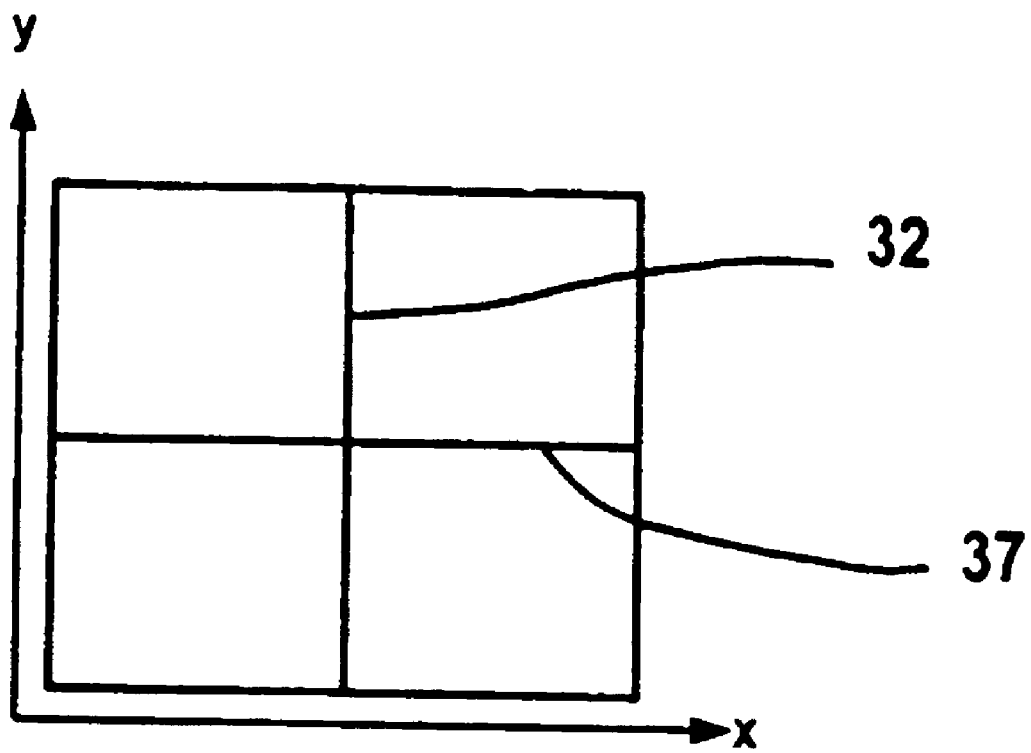
FIG. 9 shows a measurement arrangement for an abutting location in the x-direction and the y-direction.
Figure 10:
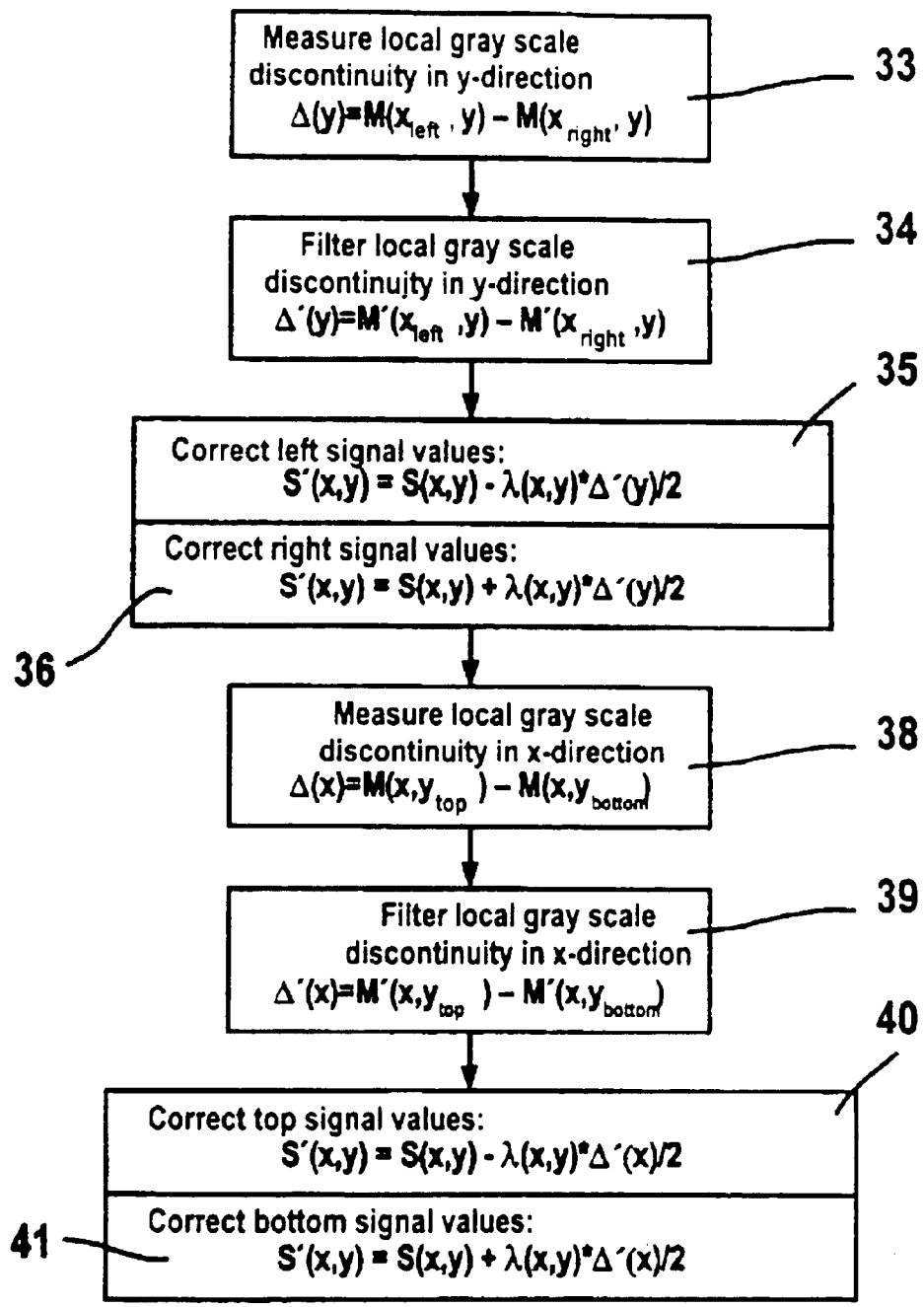
FIG. 10 is a flowchart for measurement and correction procedure for abutting locations in the x-direction and the y-direction.

A complete measurement and correction procedure for four plates 20 having abutting locations 37 in x-direction and 32 in y-direction is explained in greater detail on the basis of FIGS. 9 and 10. The above-described measurement, filtering and correction according to FIG. 8 ensues [sic] first. Subsequently, this measurement 38 is implemented in x-direction according to Equation (5).

$$\Delta(x)=M(x,y_{top})-M(x,y_{bottom}) \qquad (5).$$

A filtering of the local discontinuity in gray scale value then ensues in x-direction according to Equation (6).

$$\Delta'(x)=M'(x,y_{top})-M'(x,y_{bottom}) \qquad (6).$$

After this pre-processing, the correction 40 of the signal values first ensues above the abutting location 37 according to Equation (7):

$$S'(x,y)=S(x,y)-\lambda(x,y)*\Delta'(x)/2 \qquad (7)$$

and then (41) ensues below the abutting location 37 according to Equation (8):

$$S'(x,y)=S(x,y)+\lambda(x,y)*\Delta'(x)/2 \qquad (8).$$

Figure 11:
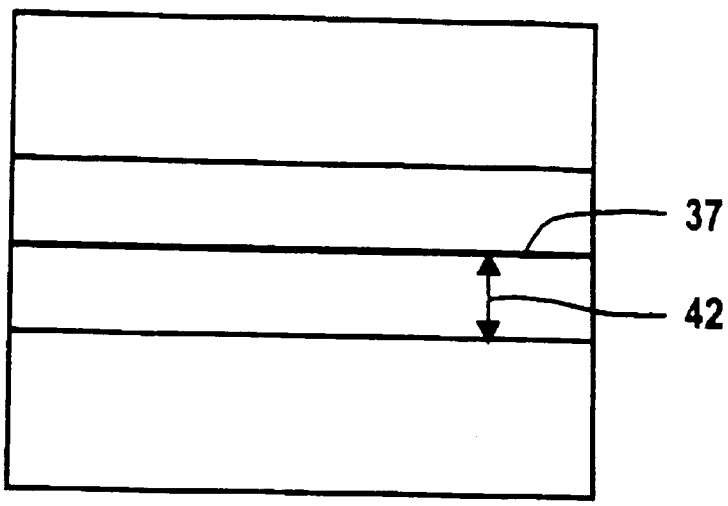
FIG. 11 is an example of correction ranges in the x-direction above and below the abutting edge.

The correction range 42 is entered in FIG. 11 at only one abutting location 37 in x-direction. This applies given the employment of two plates 20. Given four plates 20 with abutting locations 37 in the x-direction and 32 in the y-direction, the correction range in y-direction 43 is entered, this diminishing to a reduced correction range 45 in the proximity of the cross 44 of abutting edges.

Figure 13:
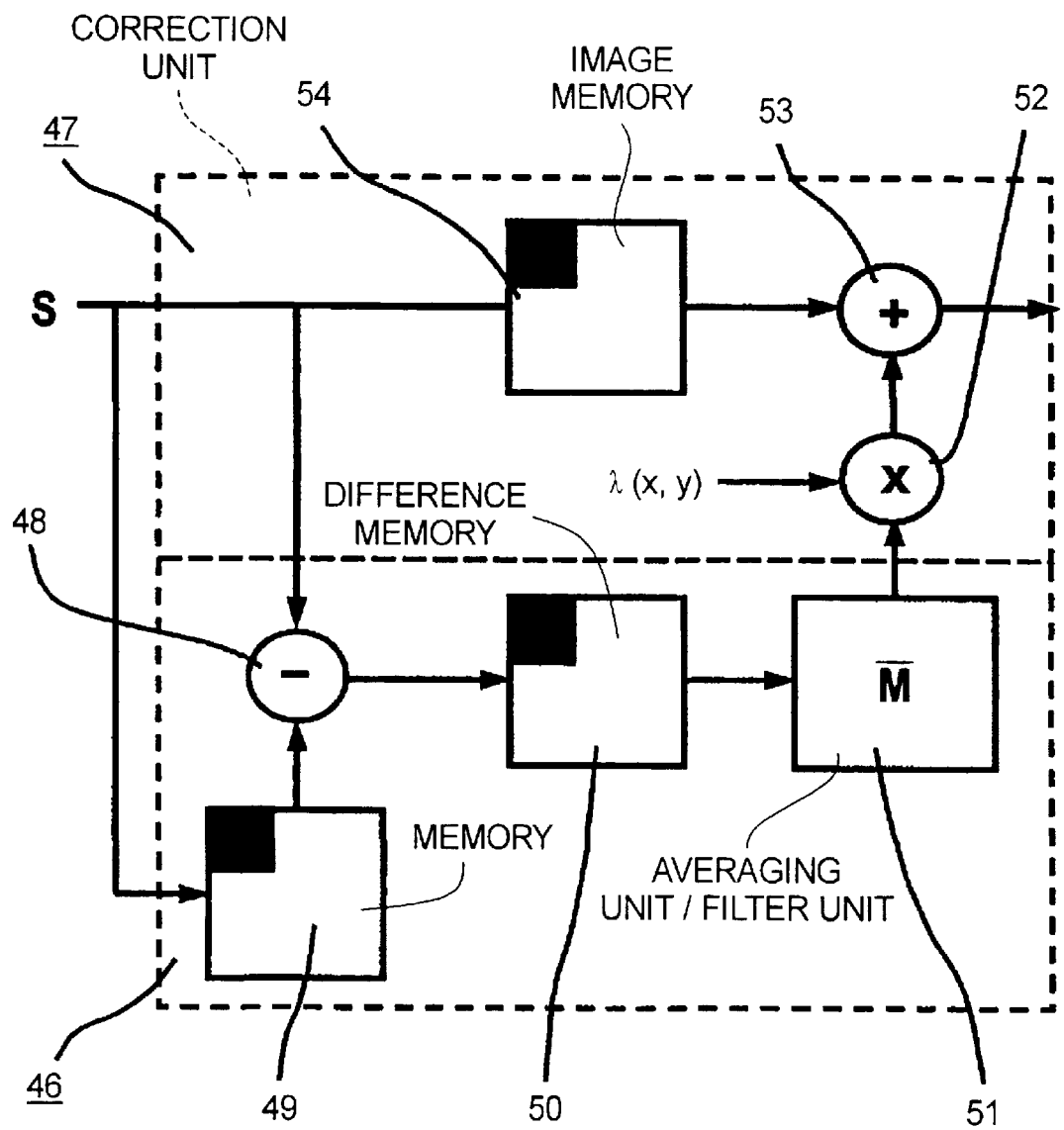
FIG. 13 is a block diagram of the inventive detection unit and correction unit.

FIG. 13 shows a detection unit 46 as well as a correction unit 47 that can be part of the image system 7. The detection unit 46 is composed of a subtraction stage 48 with which the difference between the gray scale values is formed according to step 33 or step 38. The signals to the left as well as the right of the abutting locations 32 and 37 can be edited therewith such that the signal S is read into a memory 49, so that the current signal of a pixel elements preceding the abutting location 32 is stored and the current signal value of the pixel following the abutting location 32 is subtracted from this stored value. When the abutting location lies in the x-direction, than a complete line is first stored in the memory 49 and the current signal is subsequently subtracted with pixel precision from this stored signal by the subtraction stage 48.

The output signal of the subtraction stage 48 can be stored in a difference memory 50. A filtering of the local discontinuity of the gray scale value subsequently ensues either in the y-direction or in the y-direction, for example by means of an averaging stage according to Equation (2).

The output signal of the averaging stage 51 is supplied to the correction stage 47 that comprises a multiplication stage 52 at its input. Therein, the correction signal is multiplied by a location-dependent factor $\lambda(x,y)$ that can assume values between one and zero dependent on how far away it is from the abutting locations 32 or 37 it is. The output of the multiplication stage 52 is connected to an addition stage 53 that, corresponding to its operational sign, adds the correction signal weighted in this way to an image signal S that is potentially stored in an image store 54.

The continuously changing gray scale level at the abutting locations 32 and 37 can be initially detected by the inventive apparatus, i.e. measured, and can be correspondingly corrected in a second step (i.e. locally as warranted). Overall, the acquisition and correction of the gray scale levels along an abutting location 32 or 37 can be divided into the following steps:

a) A local measurement of the gray scale level ensues by suitable averaging (mean, median or the like) of local ROIs ("regions of interest") lying opposite one another at both sides of the abutting location.

b) The averages are continuously identified and registered (stored) along the abutting edge.

c) Since local gray scale levels can occur not only due to the effect to be corrected but also due to a contrast discontinuity in the illuminated subject, a suitable filtering (for example, average, median or the like) of the locally identified gray scale levels can improve the measurement of the actual effect or compensate local mis-measurements, for example due to subject contrast.

d) The local correction of the gray scale level us subsequently implemented such that the measured, potentially filtered gray scale discontinuity in the region directly at the abutting location is corrected by subtraction of the value and the gray scale value in the regions transverse relative to the abutting location are corrected continuously decreasing—i.e. with only a certain percentage of the gray scale level.

e) A continuous transition at the abutting location arises from a discontinuous transition as a result of the method.

There are a number of possibilities for the inventive implementation, a few of these being compiled as examples:

(i) The method can be applied for an individual abutting location in x-direction or y-direction (detector, composed of 2 plates). The procedure (for an abutting location in y-direction) is shown in FIG. 3.

(ii) The method can be applied for abutting locations in x-direction or y-direction (detector, composed of 4 plates). The procedure is shown in FIG. 4.

(iii) The method can be expanded to an arbitrary number of plates and abutting locations.

(iv) The measurement of the gray scale level (left and right or, respectively, above and below the abutting location) can ensue by averaging, averaging with thresholds (for example, averaging upon exclusion of the lowest 5% and highest 5%), median or the like.

(v) The measurement of the gray scale level can refer to the pixel (left and right or, respectively, above and below the abutting location) of the abutting location or to a larger ROI composed of n×m pixels respectively left and right or above and below the abutting location.

(vi) The correction values along the abutting location derived from the measured gray scale levels can be limited in order to avoid artifacts, for example by means of a maximally permitted level, dependent on the local signal or on a global threshold.

(vii) The gray scale level along the abutting location (in y-direction or x-direction) can be "homogenized" by filtering along the abutting location (for example, averaging, averaging with thresholds, median or the like) or, respectively, can be freed of local subject contrasts.

(viii) The correction in the image region left or, respectively, right of a y-abutting location or above and below an x-abutting location is implemented with an x-dependent or y-dependent function $\lambda$. This function decreases steadily (from 1 to 0) viewed proceeding from the abutting location. This function can be described with a straight line, a polynomial or the like.

(ix) The "range" of the correction function $\lambda$ (i.e. the region from the abutting location at which the function has the value 1 up to the region at which the function has dropped to 0) is variable (for example, 500 pixels given an overall matrix of 2000×2000 pixels).

Figure 12:
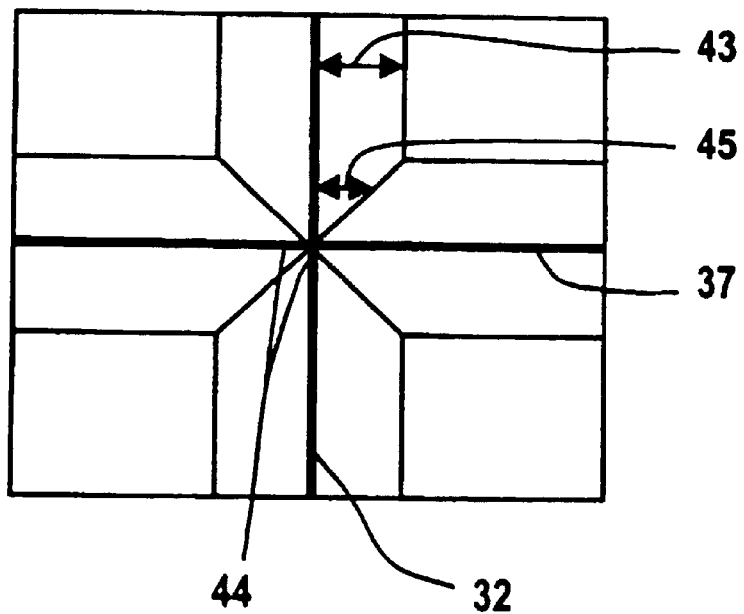
FIG. 12 shows example of correction ranges to the left and right of the abutting edge given simultaneous reduction of the range in the proximity of the cross of abutting edges.

(x) Given abutting locations in x-direction and y-direction and, therefore, corrections in x-direction and y-direction, the correction function $\lambda$ should be a function of x and y since discontinuities arise at the intersection of the abutting edges. These can be avoiding by reducing the correction range in the intersecting region (see FIG. 12).

Although modifications and changes may be suggested by those skilled in the art, it is the intention of the inventor to embody within the patent warranted hereon all changes and modifications as reasonably and properly come within the scope of his contribution to the art.

I claim as my invention:

1. An X-ray diagnostic installation comprising:
    an X-ray tube which emits an X-ray beam;
    a planar solid-state X-ray image converter on which said X-ray beam is incident, said image converter being comprised of a plurality of individual detectors abutting each other at respective abutting locations, said image converter emitting electrical signals corresponding to X-ray incident thereon, including continuously changing electrical signals at said abutting locations;
    an image system supplied with said electrical signals for converting said electrical signals into gray scale values having respective gray scale levels, and including a detection unit which locally identifies a height of continuously changing gray scale levels at said abutting locations and which generates a correction signal dependent on said height, and a correction unit, supplied with said correction signal, for continuously adapting said gray scale levels at said abutting locations within a region of said image converter; and
    a playback device which generates a visible image from said gray scale levels, said abutting locations being rendered invisible in said image due to said continuous adaption.

2. An X-ray diagnostic installation as claimed in claim 1 wherein said detection unit comprises a subtraction stage.

3. An X-ray diagnostic installation as claimed in claim 1 wherein said detection unit comprises an averaging stage.

4. An X-ray diagnostic installation as claimed in claim 1 wherein said detection unit comprises a filter stage.

5. An X-ray diagnostic installation as claimed in claim 1 wherein said correction unit comprises a multiplication stage which multiplies said correction signal from said detection unit within a region by a location-dependent multiplication factor.

6. An X-ray diagnostic installation as claimed in claim 5 wherein said image converter has an imaging region defined by an x-direction and a y-direction, and wherein said multiplication stage multiplies said correction signal by a function that steadily decreases proceeding from said abutting location, said function being selected from the group consisting of a function dependent on said x-direction and a function dependent on said y-direction.

7. An X-ray diagnostic installation as claimed in claim 5 wherein said correction unit further comprises an addition stage connected to said multiplication stage.

8. An X-ray diagnostic installation as claimed in claim 5 wherein said correction unit allows adjustment of a size of said region.

9. An X-ray diagnostic installation as claimed in claim 1 wherein said image converter comprises two individual detectors having a single abutting edge.

10. An X-ray diagnostic installation as claimed in claim 1 wherein said image converter comprises four individual detectors having two abutting edges forming a cross.

* * * * *